(12) United States Patent
Zhang et al.

(10) Patent No.: US 9,853,284 B2
(45) Date of Patent: Dec. 26, 2017

(54) GRAPHENE OXIDE AS A SULFUR IMMOBILIZER IN HIGH PERFORMANCE LITHIUM/SULFUR CELLS

(71) Applicant: THE REGENTS OF THE UNIVERSITY OF CALIFORNIA, Oakland, CA (US)

(72) Inventors: Yuegang Zhang, Cupertino, CA (US); Elton J. Cairns, Walnut Creek, CA (US); Liwen Ji, Richland, WA (US); Mumin Rao, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/498,113

(22) Filed: Apr. 26, 2017

(65) Prior Publication Data

US 2017/0294646 A1    Oct. 12, 2017

Related U.S. Application Data

(62) Division of application No. 14/347,600, filed as application No. PCT/US2012/058047 on Sep. 28, 2012, now Pat. No. 9,673,452.

(Continued)

(51) Int. Cl.
  *H01M 2/00* (2006.01)
  *H01M 4/36* (2006.01)
  (Continued)

(52) U.S. Cl.
  CPC ........... *H01M 4/364* (2013.01); *C01B 31/043* (2013.01); *C01B 31/26* (2013.01); *C07D 303/38* (2013.01);
  (Continued)

(58) Field of Classification Search
  CPC ............... H01M 4/583; H01M 2/1653; H01M 10/0566; H01M 4/625; C07D 303/38; C01B 31/26
  See application file for complete search history.

(56) References Cited

U.S. PATENT DOCUMENTS

2010/0317790 A1   12/2010  Jang et al.
2011/0052813 A1   3/2011   Ho et al.
(Continued)

FOREIGN PATENT DOCUMENTS

WF   2010074918 A1   7/2010
WO   2011016889 A2   2/2011

OTHER PUBLICATIONS

Synthesis of Graphene Oside using Modified Hummers Method: Solvent Influence, Zaaba et al., Date Unknown.*

(Continued)

*Primary Examiner* — Mark F Huff
*Assistant Examiner* — Monique Wills
(74) *Attorney, Agent, or Firm* — Womble Bond Dickinson (US) LLP

(57) ABSTRACT

The loss of sulfur cathode material as a result of polysulfide dissolution causes significant capacity fading in rechargeable lithium/sulfur cells. Embodiments of the invention use a chemical approach to immobilize sulfur and lithium polysulfides via the reactive functional groups on graphene oxide. This approach obtains a uniform and thin (~tens of nanometers) sulfur coating on graphene oxide sheets by a chemical reaction-deposition strategy and a subsequent low temperature thermal treatment process. Strong interaction between graphene oxide and sulfur or polysulfides demonstrate lithium/sulfur cells with a high reversible capacity of 950-1400 mAh $g^{-1}$, and stable cycling for more than 50 deep cycles at 0.1 C.

11 Claims, 19 Drawing Sheets

Related U.S. Application Data

(60) Provisional application No. 61/541,374, filed on Sep. 30, 2011.

(51) Int. Cl.

| | | |
|---|---|---|
| *H01M 4/587* | (2010.01) | |
| *H01M 10/0566* | (2010.01) | |
| *H01M 4/38* | (2006.01) | |
| *H01M 10/0525* | (2010.01) | |
| *C01B 31/26* | (2006.01) | |
| *C01B 31/04* | (2006.01) | |
| *C07D 303/38* | (2006.01) | |

(52) U.S. Cl.
CPC .......... *H01M 4/382* (2013.01); *H01M 4/587* (2013.01); *H01M 10/0525* (2013.01); *H01M 10/0566* (2013.01); *C01P 2002/72* (2013.01); *C01P 2002/82* (2013.01); *C01P 2002/85* (2013.01); *C01P 2002/88* (2013.01); *C01P 2004/03* (2013.01); *C01P 2004/04* (2013.01); *C01P 2006/40* (2013.01); *H01M 2300/0045* (2013.01)

(56) References Cited

U.S. PATENT DOCUMENTS

| | | |
|---|---|---|
| 2011/0219607 A1 | 9/2011 | Nanjundaswamy et al. |
| 2012/0080656 A1* | 4/2012 | Choi .................. B82Y 30/00 257/2 |
| 2012/0088154 A1 | 4/2012 | Liu et al. |
| 2013/0164635 A1 | 6/2013 | Schmidt et al. |

OTHER PUBLICATIONS

Wang, H. et al. (2011). "Graphene-Wrapped Sulfur Particles as a Rechargeable Lithium—Sulfur Battery Cathode Material with High Capacity and Cycling Stability", Nano Letters, 11:264-2647.

Ji, L. et al. (2011). "Graphene Oxide as a Sulfur Immobilizer in High Performance Lithium/Sulfur Cells", JACS 133:18522-18525.

Cao, Y. et al. (2011). "Sandwich-Type Functionalized Graphene Sheet-Sulfur Nanocomposite for Rechargeable Lithium Batteries", Phys. Chem. Chem. Phys. 13:7660-7665.

International Search Report and Written Opinion for PCT Application No. PCT/US2012/058047, filed Sep. 28, 2012, 6 pages.

Vol. 11, No. 7, (Jun. 24, 2011) pp. 2644-2647, Retrieved from the Internet: URL:http://pubs.acs.org/doi/abs/10.1021/n1200658a.

European Extended Search Report for European Application No. 12835530.2, dated May 15, 2015, 8 pages.

Second Notification of Office Action for Chinese Application 201280054690.8, dated Aug. 24, 2016, 8 pages.

First Notification of Office Action for Chinese Application 201280054690.8, dated Nov. 23, 2015, 8 pages.

\* cited by examiner

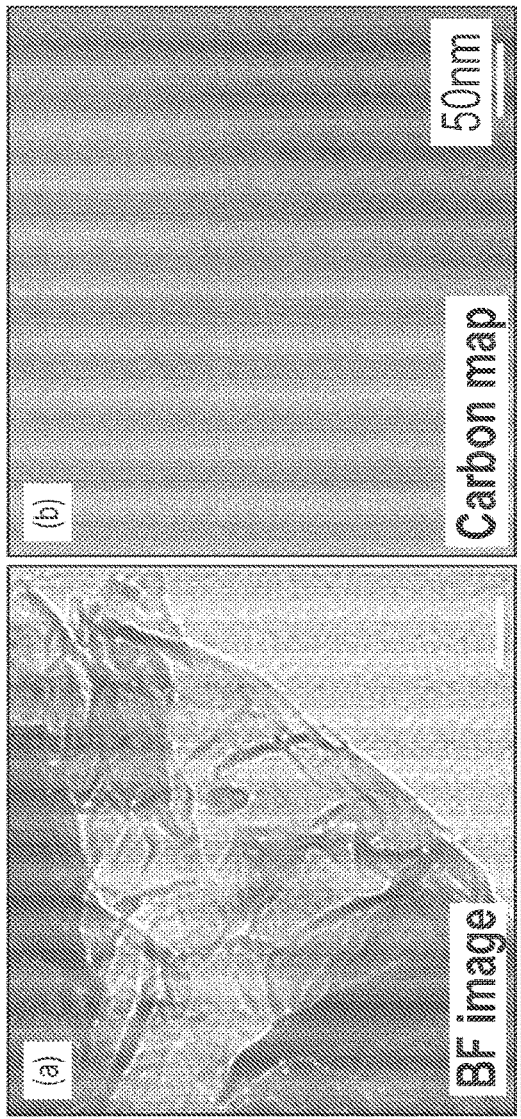
FIG. 2A
FIG. 2B
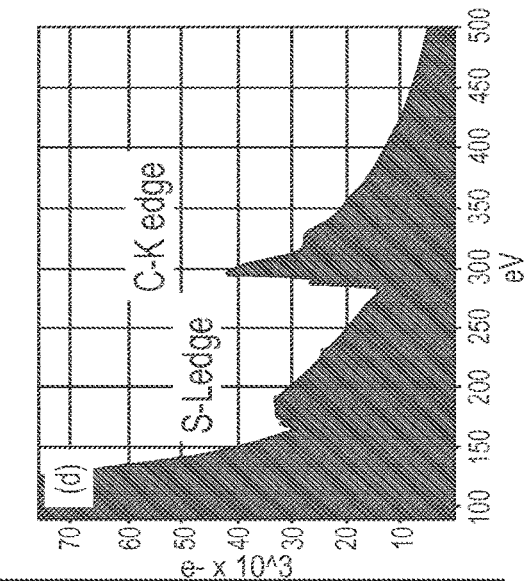
FIG. 2D
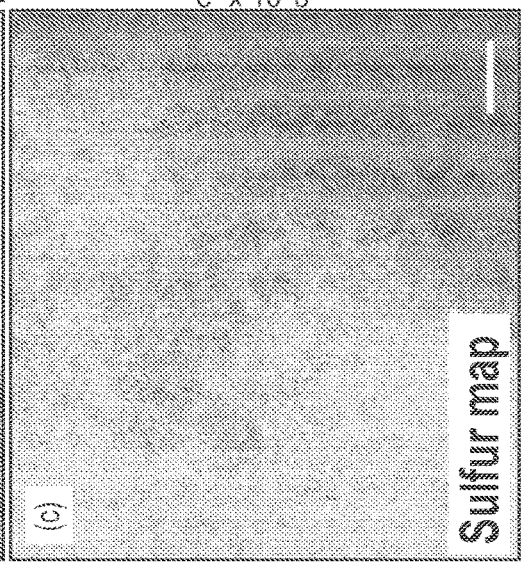
FIG. 2C

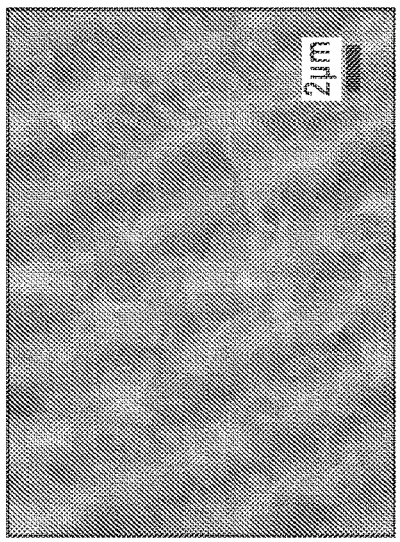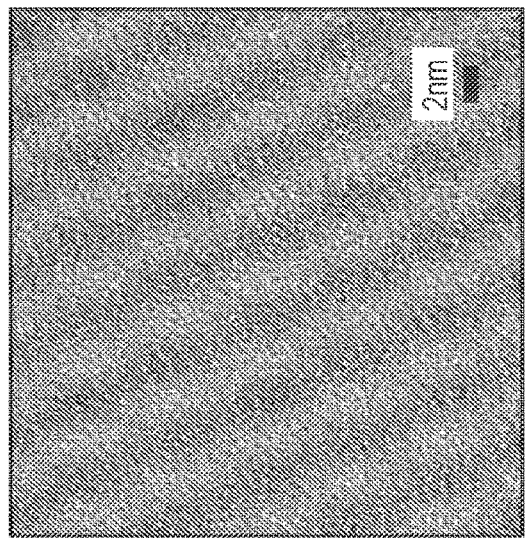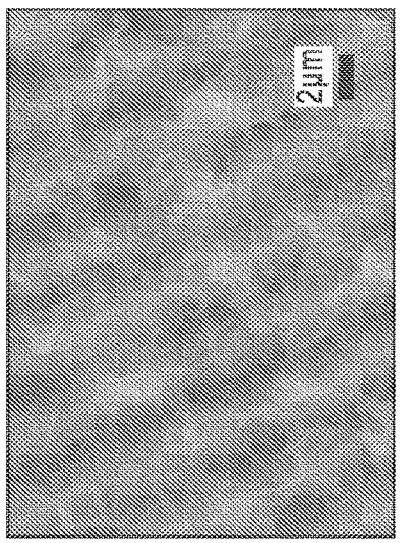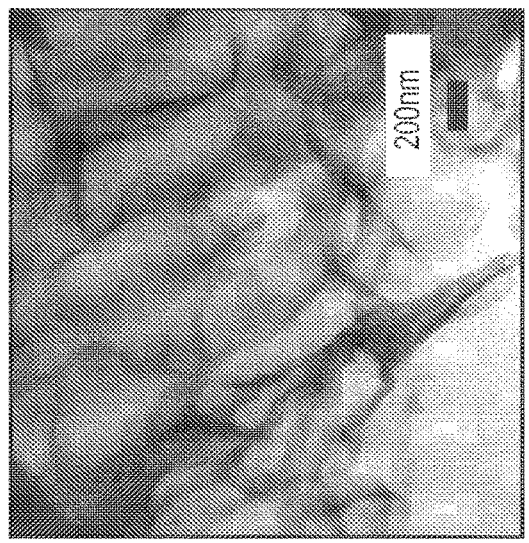
FIG. 17A
FIG. 17B
FIG. 17C
FIG. 17D

GRAPHENE OXIDE AS A SULFUR IMMOBILIZER IN HIGH PERFORMANCE LITHIUM/SULFUR CELLS

CROSS REFERENCE TO RELATED APPLICATIONS

This is a divisional of U.S. patent application Ser. No. 14/347,600, filed Mar. 26, 2014, which is a US National Stage 371 of PCT International Application No.: PCT/US12/58047, filed Sep. 28, 2012, which claims priority to U.S. Provisional Application Ser. No. 61/541,374 filed Sep. 30, 2011, which are incorporated herein by reference as fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

Field of the Invention

Elemental sulfur (S) is very attractive as a cathode material for high-specific-energy rechargeable lithium batteries, because a battery based on the lithium/sulfur (Li/S) couple would yield a theoretical specific capacity of about 1675 mAh $g^{-1}$ with a theoretical specific energy of 2600 Wh $kg^{-1}$ on the assumption of the complete reaction of Li with S to form $Li_2S$. In addition, S is also inexpensive, abundant and nontoxic. Therefore, S is a promising cathode material for high-energy-density Li/S batteries. Despite these considerable advantages, there are still a number of challenges in Li/S batteries. The first one is the high electrical resistivity of elemental S. The second one is the high solubility (in organic solvent electrolytes) of the polysulfide ions that are formed during the discharge/charge processes. The soluble intermediate Li polysulfides can diffuse through the electrolyte to the Li anode where they are reduced to form solid precipitates (such as $Li_2S$ or $Li_2S_2$). These reduced products can also diffuse back to the cathode during recharging. These issues can lead to low active materials utilization, low coulombic efficiency, and short cycle life of the S electrode. In order to address these challenges, various carbon and conductive polymer materials have been used to accommodate S and so to overcome its insulating property and reduce the dissolution of Li polysulfides, as reported by Nazar, et al. and others. The most recent work by Archer et al. demonstrated that the mesoporous carbon (C)/S nanocomposites can be cycled for 100 cycles at 974 mAh $g^{-1}$ at a rate of 0.5 C with the corresponding coulombic efficiency of about 96% and 94%, respectively, at the $1^{st}$ and $100^{th}$ cycles. Despite this progress, there are still few reports on fabricating novel C—S cathodes via a chemical reaction-deposition method.

BRIEF DESCRIPTION OF THE DRAWINGS

The foregoing aspects and others will be readily appreciated by the skilled artisan from the following description of illustrative embodiments when read in conjunction with the accompanying drawings.

FIG. 2A illustrates a transmission electron microscope (TEM) bright field (BF) image.

FIG. 2B illustrates a corresponding elemental mapping for carbon

FIG. 2C illustrates a homogeneous S coating on the GO flakes.

FIG. 2D illustrates an electron energy-loss spectrum (EELS) according to an embodiment of the invention.

FIG. 17A illustrates a SEM image of the as-synthesized GO—S nanocomposites after heat treatment in Ar at 160° C. for 12 hours according to an embodiment of the invention.

FIG. 17B illustrates another SEM image of the as-synthesized GO—S nanocomposites after heat treatment in Ar at 160° C. for 12 hours according to an embodiment of the invention.

FIG. 17C illustrates a TEM image of the as-synthesized GO—S nanocomposites after heat treatment in Ar at 160° C. for 12 hours according to an embodiment of the invention.

FIG. 17D illustrates another TEM image of the as-synthesized GO—S nanocomposites after heat treatment in Ar at 160° C. for 12 hours according to an embodiment of the invention.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Figure 1A:
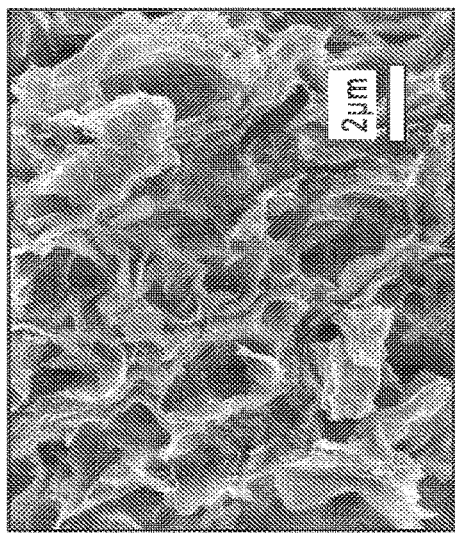
FIG. 1A illustrates a scanning electron microscope (SEM) image of a graphene oxide-sulfur (GO—S) nanocomposite after heat treatment in argon (Ar) at 155° C. for 12 hours according to an embodiment of the invention.
Figure 1B:
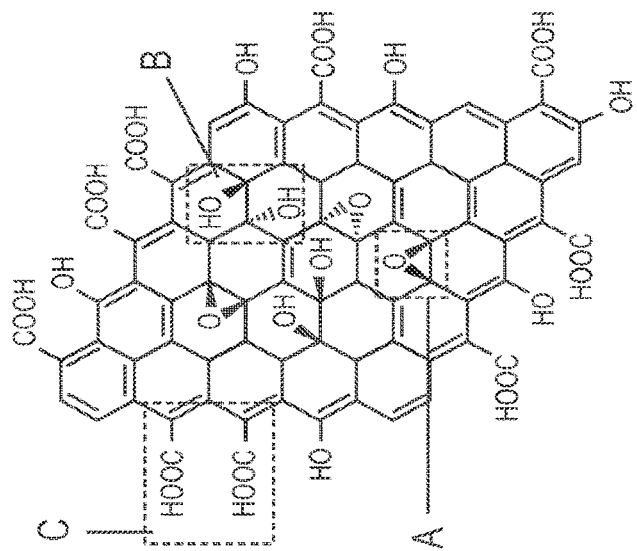
FIG. 1B illustrates the structure and properties of graphite oxide (GO) according to an embodiment of the invention.

Various embodiments of the invention describe a low cost and environmentally benign chemical reaction-deposition method to immobilize sulfur (S) on quasi-2-dimensional graphene oxides (GO) to prepare graphene oxide-sulfur (GO—S) nanocomposite cathodes for Li/S cells in ionic liquid-based electrolytes. FIG. 1a shows a scanning electron microscope (SEM) image of a GO—S nanocomposite. FIG. 1b illustrates the structure and properties of graphene oxide (GO) which may depend on a particular synthesis method and degree of oxidation. The illustrated GO structure comprises functional groups including a) epoxy bridges, b) hydroxyl groups, and c) pairwise carboxyl groups. GO typically preserves the layer structure of the parent graphite, but the layers are buckled and the interlayer spacing is about two times larger (~0.7 nm) than that of graphite. Strictly speaking "oxide" is an incorrect but historically established name. Besides oxygen epoxide groups (bridging oxygen atoms), other functional groups experimentally found are: carbonyl (═CO), hydroxyl (—OH), and phenol groups attached to both sides. There is evidence of "buckling" (deviation from planarity), folding and cracking of graphene oxide sheets upon deposition of the layers on a choice of substrate.

In one embodiment, nano-S was deposited onto graphene oxide (GO) sheets by a chemical reaction-deposition method (see below experimental details section for further details). Then, the as-synthesized samples were heat treated in an argon (Ar) environment at low temperature (155° C.) for 12 hours in order to remove some of the bulk S which is not directly attached to the GO layers. When the as-synthesized GO—S nanocomposites were heat-treated in Ar, the bulk S on the external surface of the GO melted and diffused into the pores of the GO due to the strong adsorption effects derived from both the high surface area and the functional groups on the surface of the GO. At the same time, this low-temperature heat treatment process can partially remove and/or chemically modify some of the functional groups on the GO surface and improve the electronic conductivity of the as-prepared GO—S nanocomposites (See Table 1 below, wherein these materials were heat treated in Ar environment at 155° C. for 12 hour).

TABLE 1

Conductivities of the prepared materials.

| | Sample name | | |
|---|---|---|---|
| | GO | Heat treated GO | Heat treated GO-S nanocomposites |
| Conductivity (S cm$^{-1}$) | 0.00129 | 0.316 | 0.105 |

Figure 1C:
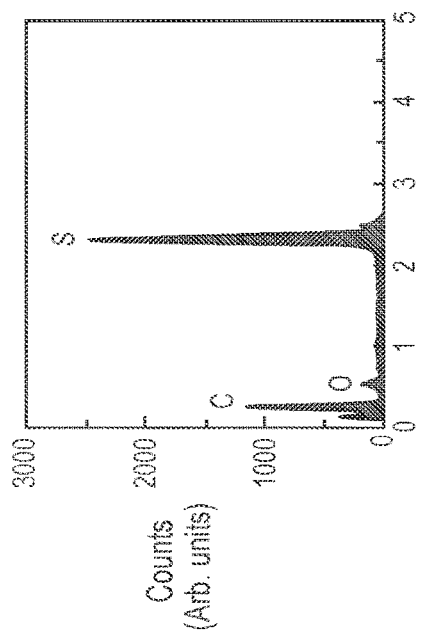
FIG. 1C illustrates an energy-dispersive X-ray (EDX) spectrum of the GO—S nanocomposite after heat treatment in Ar at 155° C. for 12 hours according to an embodiment of the invention.
Figure 5:
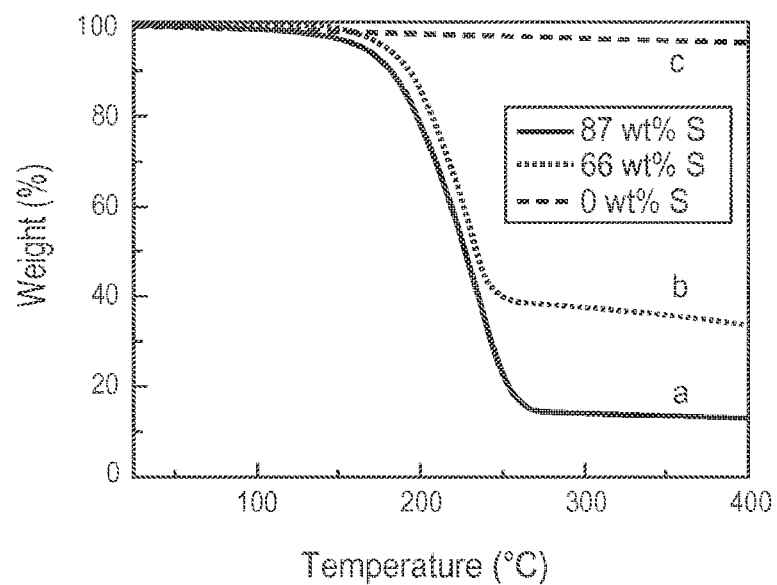
FIG. 5 illustrates a thermo gravimetric analysis (TGA) curve of GO—S nanocomposite recorded in $N_2$ with a heating rate of 10° C. $min^{-1}$ before (a) and after (b) heat treatment in Ar environment at 155° C. for 12 hours; (c) Pure GO after heat treatment in Ar environment at 155° C. for 12 hours according to an embodiment of the invention.

FIG. 1a shows the SEM image of the as-prepared GO—S nanocomposite after heat treatment. The layer-like extremely conjugated nanostructures with a highly developed porous structure are clearly illustrated. The energy-dispersive X-ray (EDX) microanalysis in FIG. 1c confirms the existence of S in the composites. As indicated in a thermo gravimetric analysis (TGA), about 66 wt % S is incorporated into the GO after heat treatment. FIG. 5 illustrates a TGA curve of GO—S nanocomposite recorded in $N_2$ with a heating rate of 10° C. $min^{-1}$ before (a) and after (b) heat treatment in Ar environment at 155° C. for 12 hours; (c) Pure GO after heat treatment in Ar environment at 155° C. for 12 hours. From the TGA result (c), it is clear that the mass loss due to the loss of functional groups from the pure GO after heat treatment in Ar environment at 155° C. for 12 hours is very small (~3%). The mass loss due to the loss of functional groups from GO—S upon heating GO—S nanocomposites should be even smaller. Therefore, we are able to calculate the S content of the GO—S nanocomposite using the TGA data according to an embodiment of the invention.

Figure 6B:
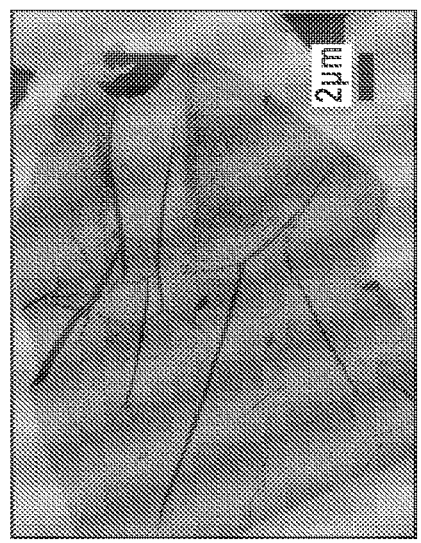
FIG. 6B illustrates another SEM image for pure GO according to an embodiment of the invention.
Figure 6A:
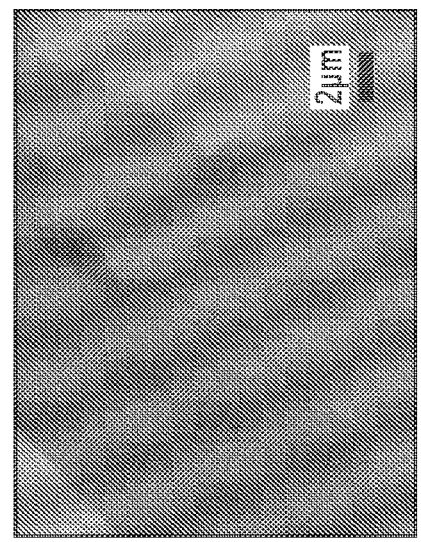
FIG. 6A illustrates a SEM image for pure GO according to an embodiment of the invention.
Figure 7A:
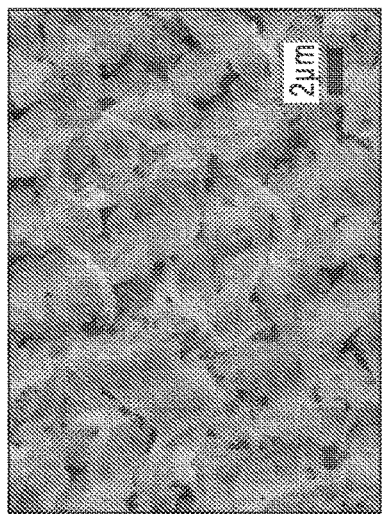
FIG. 7A illustrates a SEM image of the as-prepared GO—S nanocomposites before heat treatment according to an embodiment of the invention.
Figure 7B:
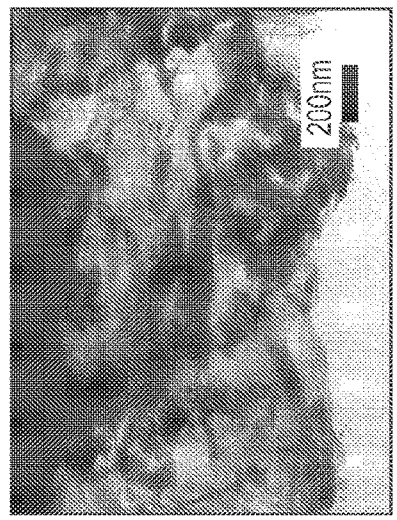
FIG. 7B illustrates another SEM image of the as-prepared GO—S nanocomposites before heat treatment according to an embodiment of the invention.
Figure 7C:
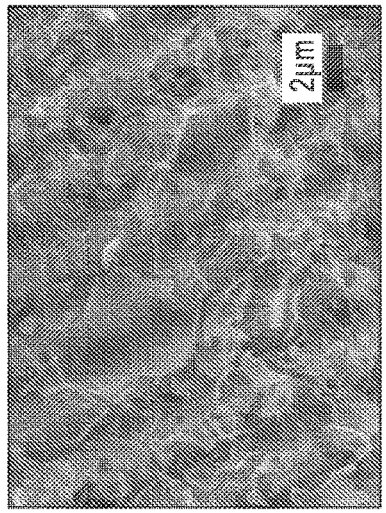
FIG. 7C illustrates a TEM image for GO—S nanocomposites before heat treatment according to an embodiment of the invention.
Figure 7D:
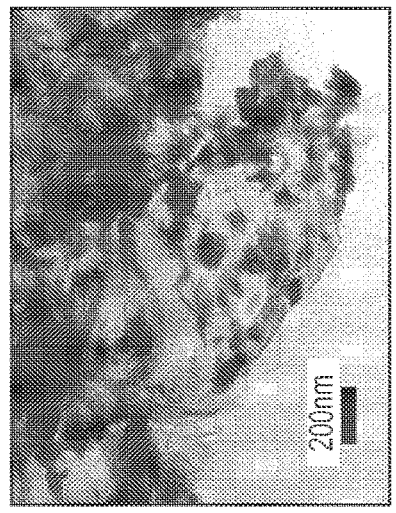
FIG. 7D illustrates another TEM image for GO—S nanocomposites before heat treatment according to an embodiment of the invention.

The transmission electron microscope (TEM) image in FIG. 2a and the electron energy-loss spectrum (EELS) in FIG. 2d indicate that a thin layer of S with a thickness of tens of nanometers is homogenously dispersed on the flake-like GO surface with no significant fraction of bulk S exposed on the external surface of the sample after heat treatment (For comparison, see the FIGS. 6a,b SEM images for pure GO and FIGS. 7a,b SEM images and FIGS. 7c,d TEM images for GO—S nanocomposites before heat treatment). The corresponding elemental mapping of carbon (FIG. 2b), and S (FIG. 2c) display a very similar intensity distribution, revealing a homogeneous S coating on the GO flakes in the as-formed GO—S nanocomposites.

Figure 9:
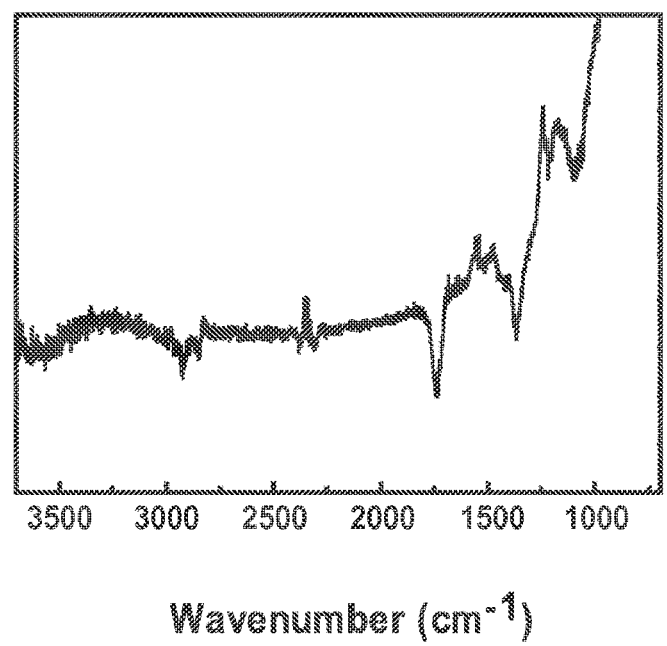
FIG. 9 illustrates attenuated total reflection Fourier transform infrared spectroscopy (ATR-FTIR) spectra of GO according to an embodiment of the invention.
Figure 10A:
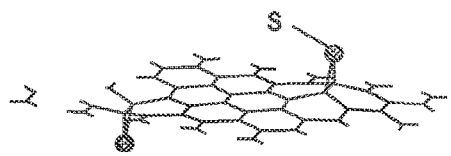
FIG. 10A illustrates a configuration of two S atoms adsorption on graphene separately according to one embodiment of the invention.
Figure 10B:
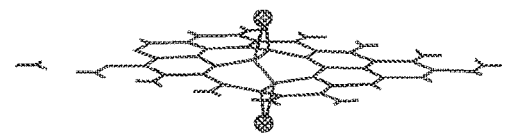
FIG. 10B illustrates a configuration of two S atoms adsorption on graphene in pair according to one embodiment of the invention.
Figure 10C:
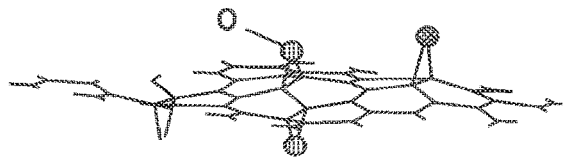
FIG. 10C illustrates an adsorption configuration according to an embodiment of the invention.
Figure 10D:
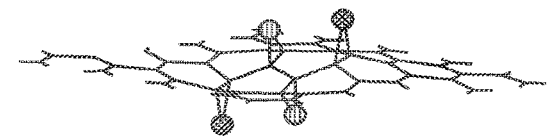
FIG. 10D illustrates another adsorption configuration according to an embodiment of the invention.
Figure 10E:
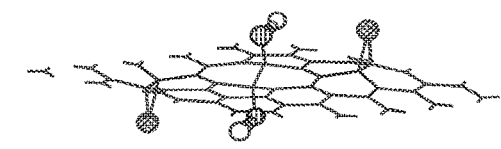
FIG. 10E illustrates yet another adsorption configuration according to an embodiment of the invention.
Figure 10F:
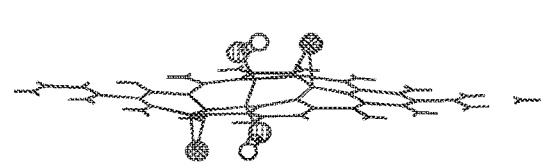
FIG. 10F illustrates yet another adsorption configuration according to an embodiment of the invention
Figure 10G:
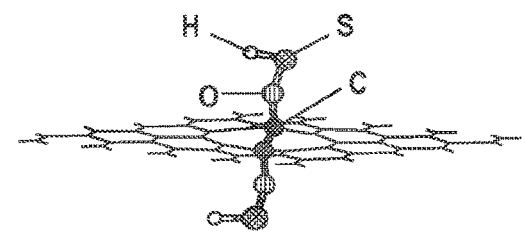
FIG. 10G illustrates yet another adsorption configuration according to an embodiment of the invention.

The unique structure of the GO—S nanocomposite can improve the overall electrochemical performance when it is used as a cathode material for Li/S batteries. Firstly, it can accommodate the significant volume changes of the S as it is converted to $Li_2S$ on discharge, and back to elemental S on recharge. In addition, the partially reduced GO with its large surface area along with ubiquitous cavities can establish more intimate electronic contact with the S and avoid their aggregation and loss of electrical contact with the current collector. Secondly, the low-temperature heat-treated GO still contains various types of functional groups. FIG. 9 illustrates ATR-FTIR spectra of GO. The bands at 1103 $cm^{-1}$, 1226 $cm^{-1}$, and 1751 $cm^{-1}$ can be assigned to C—O stretching vibrations, C—OH stretching vibrations, and C=O stretching vibrations from carbonyl/carboxylic groups, respectively. The GO was heat treated in Ar at 155° C. for 12 hours. These functional groups can have strong adsorbing ability to anchor S atoms and to effectively prevent the subsequently formed Li polysulfides from dissolving in the electrolyte during cycling.

Figure 3A:
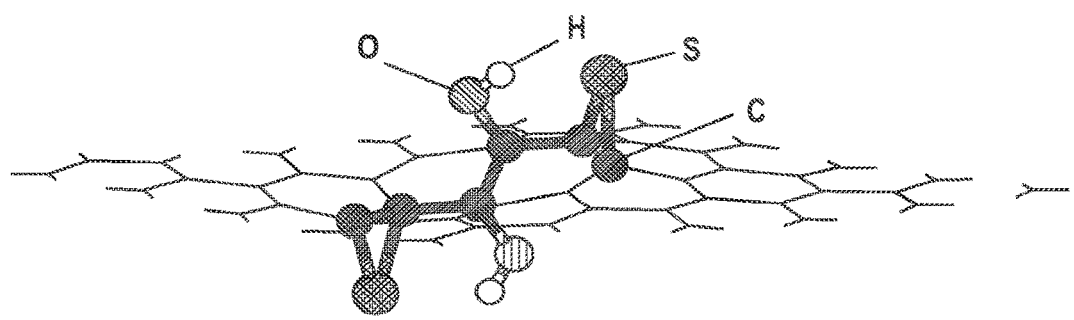
FIG. 3A illustrates a representative pattern of GO immobilizing S according to an embodiment of the invention.
Figure 3B:
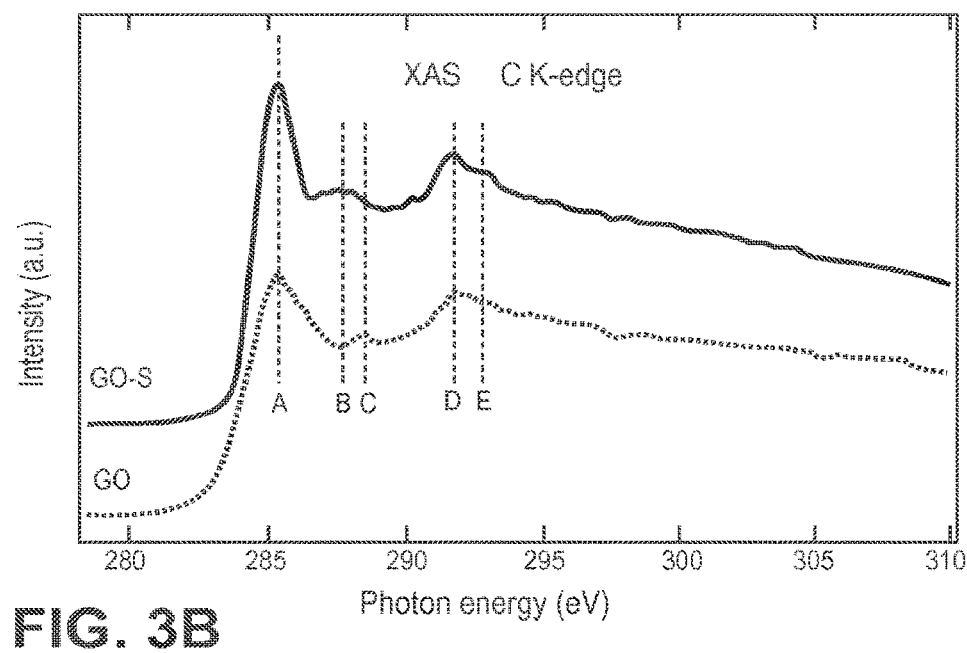
FIG. 3B shows the carbon K-edge absorption spectra according to one embodiment.

Calculations were performed, ab initio, to clarify the role of functional groups on GO in immobilizing S (see the calculation methods and detailed results section below). The results indicated that both epoxy and hydroxyl groups can enhance the binding of S to the C—C bonds due to the induced ripples by the functional groups (see FIG. 3a). We also performed a soft X-ray absorption spectroscopy (XAS) measurement which probes unoccupied electronic structure and thus is a powerful tool for probing chemical bonding in surface chemistry. FIG. 3b shows the carbon K-edge absorption spectra for both GO and GO—S nanocomposites (see also S L-edge spectrum in FIG. 11). The absorption features "A", "D" and "E", which can be attributed to the π* state, excitonic state, and σ* state, respectively, are observed for both samples. Of note in the spectra is the increase in the sharpness of the π* and excitonic state for GO—S nanocomposites as compared with GO, suggesting that the ordering of the $sp^2$-hybridized carbon structure is better formatted after S is incorporated. In addition, feature "C" originating from different functional groups (possibly C—O bond) on the GO are weakened significantly when incorporated with S, which means a strong chemical interaction between S and functional groups of GO happens and S can partially reduce the GO. In addition, a new feature "B" originated from the C—S σ* excitations, is observed for the GO—S nanocomposites.

We evaluated the electrochemical Li storage capability of these heat-treated GO—S nanocomposites as potential cathode materials for Li/S cells in the n-methyl-(n-butyl) pyrrolidinium bis(trifluoromethanesulfonyl)imide ($PYR_{14}TFSI$), Li bis(trifluoromethylsulfonyl)imide (LiTFSI), and poly(ethylene glycol) dimethyl ether (PEGDME, $M_w$=250) mixture-based electrolyte.

Figure 4A:
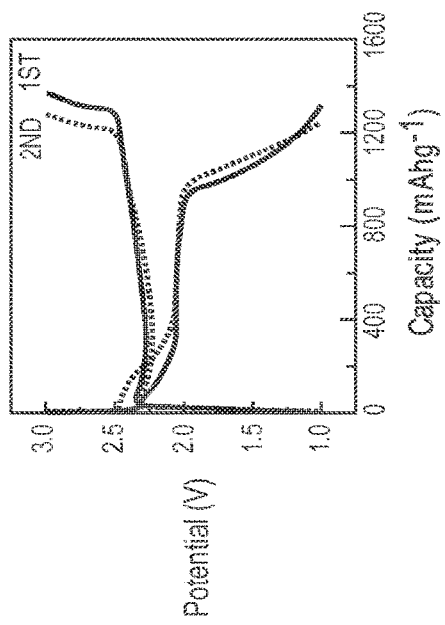
FIG. 4A illustrates cyclic voltammetry (CV) curve at 0.05 mV $s^{-1}$ scanning rate.

FIG. 4(a) shows the cyclic voltammetry (CV) profile of one electrode. The measurement was conducted at a scan rate of 0.05 $mVs^{-1}$ in the voltage range of 1.0 to 3.6V vs $Li/Li^+$. During the first cathodic scan, three main reduction peaks at around 2.4, 2.1, and 1.8 V were clearly shown. According to the reported mechanisms for oxidation and reduction of S during discharge/charge, the peak at around 2.4V can be assigned to the reduction of elemental S to higher-order Li polysulfides ($Li_2S_n$, n≥8). The peak at about 2.1 V probably corresponds to the reduction of higher-order Li polysulfides to lower-order Li polysulfides (such as $Li_2S_6$, $Li_2S_4$) from $Li_2S_8$. The peak at 1.8V is related to the reduction of polysulfide species to form $Li_2S$.

In the subsequent anodic scan, only one sharp oxidation peak is observed at about 2.6V that is attributed to the complete conversion of $Li_2S$ and polysulfides into elemental S. The main reduction peak is shifted to slightly higher potential and the oxidation peaks to lower potentials with increase in cycle number, indicating an improvement of reversibility of the cell with cycling. In addition, as the cycle number increased, the oxidation peak at 2.6V becomes less significant, while another new one at 2.35 V grows higher in intensity. The oxidation peak at 2.35V is associated with the formation of $Li_2S_n$ (n>2). After the second cycle, both the CV peak positions and peak currents undergo very small changes, indicating relatively good capacity retention. The CV results show that GO can help to prevent S from dissolving into the electrolyte because of its large surface along with some functional groups on the surface.

Figure 4B:
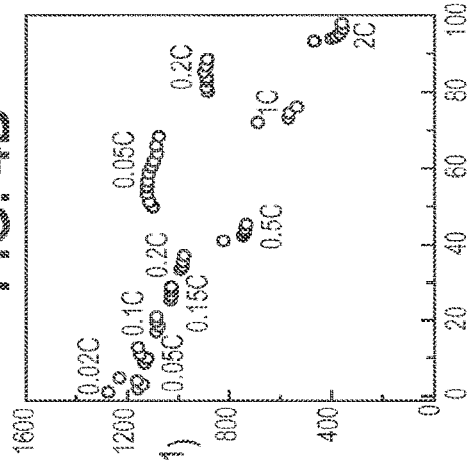
FIG. 4B illustrates galvanostatic discharge/charge profiles at 0.02 C rate.

FIG. 4(b) depicts the first and second cycle discharge/charge typical voltage profiles of the electrodes at the 0.02 C rate (1 C=1675 mA $g^{-1}$) between 1.0 and 3.0V (The capacity values in this description are calculated according to the mass of S). All the discharge curves show three plateaus in the voltage profile that are consistent with the peaks in the CV and are also well documented in the literature. The GO—S nanocomposite delivers a high initial discharge capacity of about 1320 mAh $g^{-1}$ at 0.02 C. The corresponding coulombic efficiency in the first discharge/charge cycle is 96.4%. At the second cycle, a large reversible capacity of about 1247 mAh $g^{-1}$ is preserved (97.5% coulombic efficiency), corresponding to about 94.5% capacity retention. This initial capacity loss is small compared to the formerly reported results of similar materials.

Figure 4C:
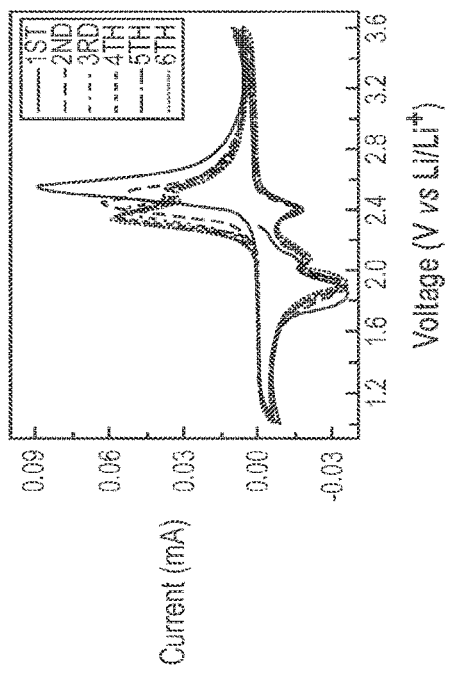
FIG. 4C illustrates cycling performance at a constant current rate of 0.1 C after an initial activation processes at 0.02 C for 2 cycles.
Figure 14:
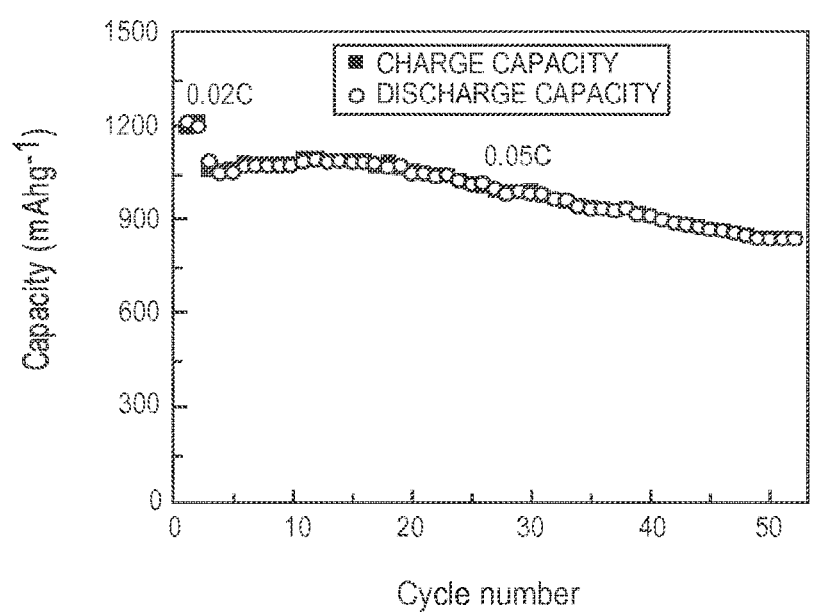
FIG. 14 illustrates cycling performance of GO—S nanocomposite cathode at a constant rate of 0.05 C after an initial activation processes at 0.02 C for 2 cycles according to an embodiment of the invention

FIG. 4(c) shows the cycling performance of the same cell cycled at a rate of 0.1 C after the initial 2 cycles at 0.02 C. The discharge capacity of the first cycle at 0.1 C remains at around 1000 mAh $g^{-1}$. At the second cycle at 0.1 C, this value decreases to about 950 mAh $g^{-1}$. However, after more than 50 cycles at the same rate, the reversible capacity remains at 954 mAh $g^{-1}$ (with a coulombic efficiency of about 96.7%), indicating very stable reversibility of the electrochemical reactions and excellent capacity retention. The cycle performance of another coin cell is further illustrated in FIG. 14. The cycling performance of GO—S nanocomposite cathode at a constant rate of 0.05 C after an initial activation processes at 0.02 C for 2 cycles. The GO—S nanocomposite was heat treated in Ar at 155° C. for 12 hours. The S content of the GO—S nanocomposite was 66 wt %, and the S content of the cathode (including carbon black and binder) was 46.2 wt %. In sum, the GO—S nanocomposites display improved coulombic efficiencies compared to former reports.

Figure 4D:
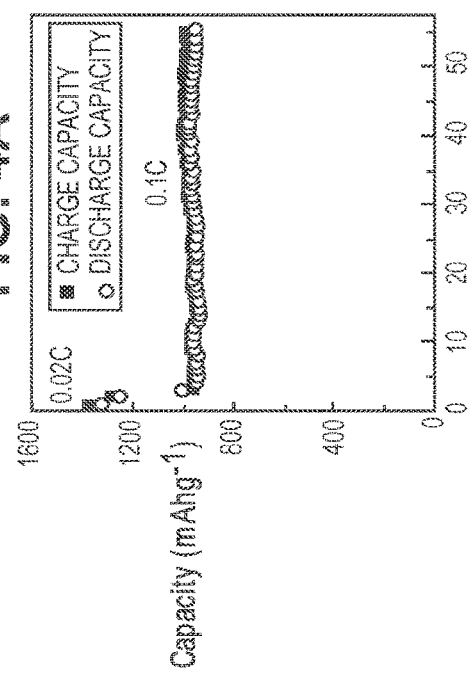
FIG. 4D illustrates reversible capacity vs. current density according to an embodiment.

The discharge capacity of the GO—S was highly reproducible over many coin cells. Another example of the electrochemical performance of the GO—S electrode is demonstrated in FIG. 4(d) where a cell showed a reversible capacity of 735 mAh $g^{-1}$ at 0.5 C after 40 cycles at various rates. Further cycling at a low rate of 0.05 C brings it back to a reversible capacity of about 1100 mAh $g^{-1}$ for another 20 cycles. When this coin cell was discharged at a higher rate of 1 C, a reversible capacity of about 550 mAh $g^{-1}$ was obtained. The last decrease of the rate to 0.2 C, yielded a reversible capacity of about 890 mAh $g^{-1}$. When this coin cell was further discharged at 2 C, an acceptable reversible capacity of about 370 mAh $g^{-1}$ was obtained, indicating excellent capacity reversibility and high rate performance even after 100 cycles.

Figure 15:
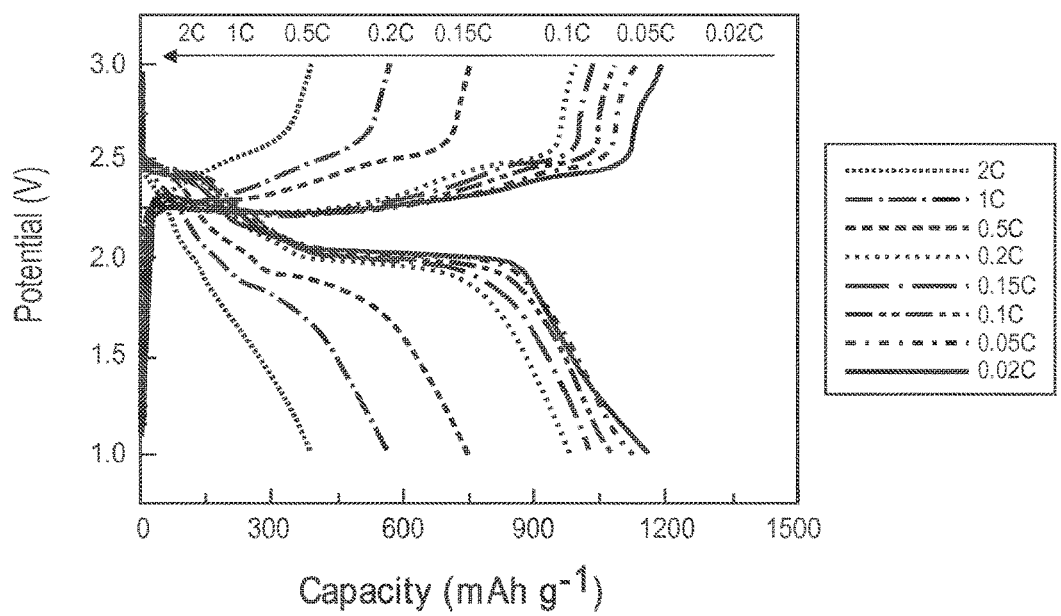
FIG. 15 illustrates a typical discharge/charge profiles (potential vs. capacity) at various C rates for GO—S nanocomposite cathode according to an embodiment of the invention.

FIG. 15 illustrates a typical discharge/charge profiles (potential vs. capacity) at various C rates for GO—S nanocomposite cathode. The GO—S nanocomposites were heat treated in Ar at 155° C. for 12 hours. The S content of the GO—S nanocomposite was 66 wt %, and the S content of the cathode (including carbon black and binder) was 46.2 wt %.

The GO clearly performs very well as a means to stabilize the S electrode. The GO provides highly reactive functional groups on its surface that can serve as immobilizers to hold the S. Also by limiting the concentration of the polysulfide anions in the electrolyte, the redox shuttle phenomenon is largely avoided. The intimate contact of the S provided by the large surface area and the functional groups on GO is favorable to good electron/ion accessibility, leading to enhanced cycle performance and rate capability. In addition, the optimized ionic liquid-based electrolytes which have suitable viscosities and wetting properties influence the penetration of electrolyte into the S electrode structure, while increasing the ionic conductivity within the electrodes at the same time.

Figure 16:
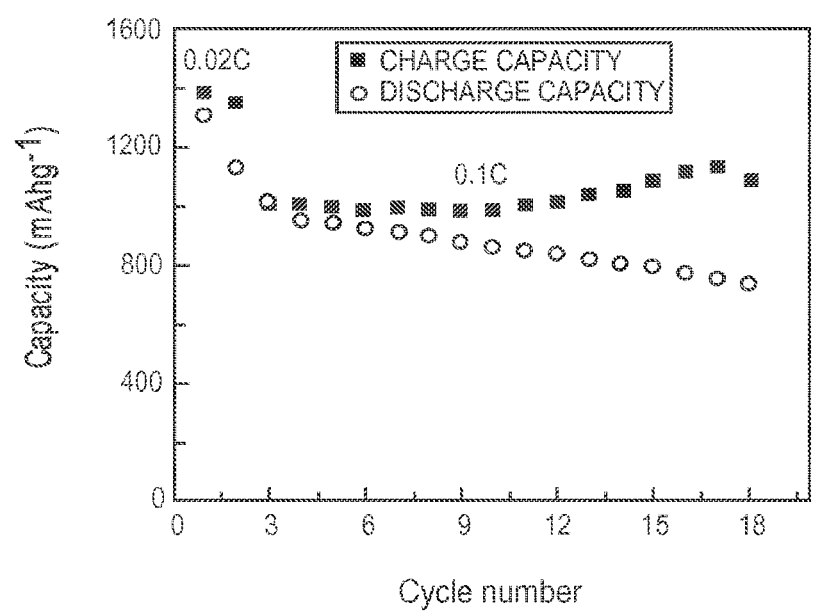
FIG. 16 illustrates a cycling performance of GO—S nanocomposite cathode at a constant rate of 0.1 C after an initial activation processes at 0.02 C for 2 cycles according to an embodiment of the invention.
Figure 18A:
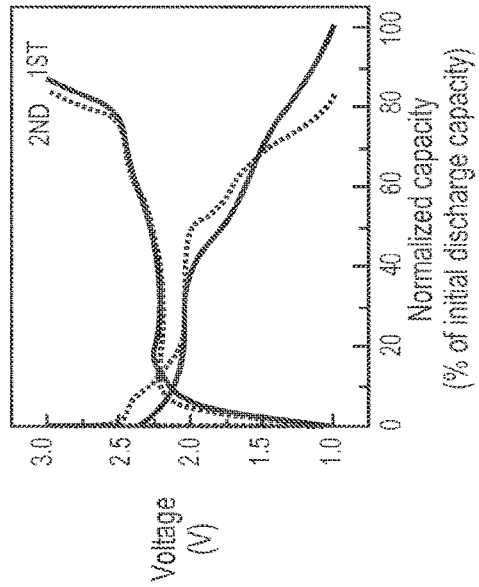
FIG. 18A illustrates a CV curve of a GO—S nanocomposite cathode at 0.05 mV s$^{-1}$ scanning rate according to an embodiment of the invention.
Figure 18B:
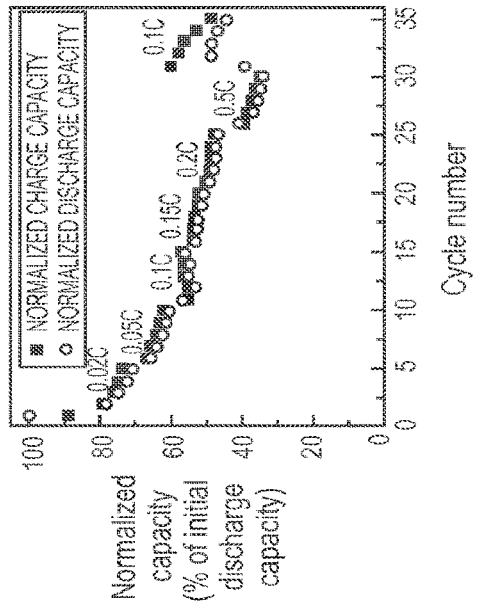
FIG. 18B illustrates galvanostatic charge/discharge profiles of GO—S nanocomposite cathode at 0.02 C rate according to an embodiment of the invention.
Figure 18C:
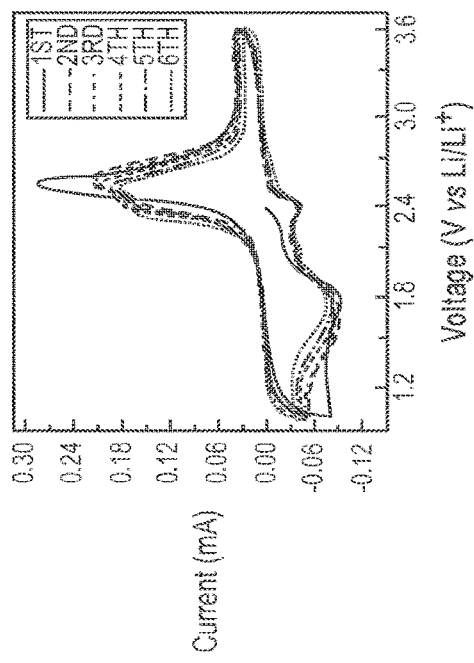
FIG. 18C illustrates cycling performance of GO—S nanocomposite cathode at a constant current rate of 0.1 C after an initial activation processes at 0.02 C for 2 cycles according to an embodiment of the invention.
Figure 18D:
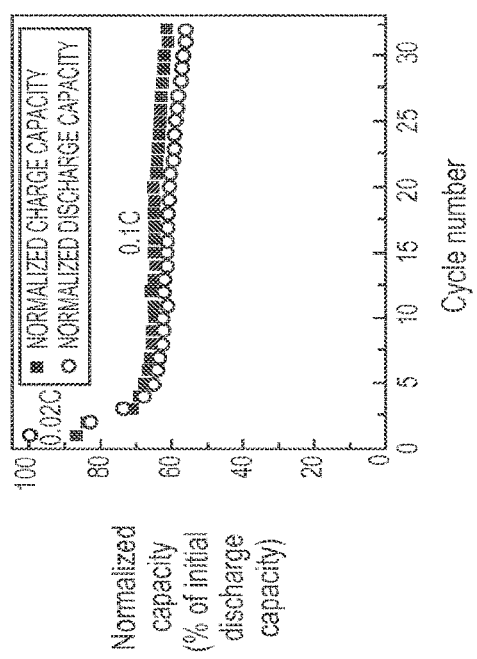
FIG. 18D illustrates reversible capacity vs. current density (rate capability) for GO—S nanocomposite cathode. All the cells were cycled in the potential window from 1.0 to 3.0 V according to an embodiment of the invention.

A control experiment in LiTFSI-PEGDME-based electrolyte is described in relation to FIG. 16 which illustrates a cycling performance of GO—S nanocomposite cathode at a constant rate of 0.1 C after an initial activation processes at 0.02 C for 2 cycles. The GO—S nanocomposites were heat treated in Ar at 155° C. for 12 hours.

From FIG. 16, we can see that the GO—S nanocomposite cathode has a very high initial reversible capacity of about 1304 mAh $g^{-1}$ at 0.02 C with the corresponding coulombic efficiency of about 94.7% in the LiTFSI-PEGDME electrolyte. After two cycles' activation at 0.02 C, a large discharge capacity of about 1014 mAh $g^{-1}$ still can be delivered at the first cycle at 0.1 C with a corresponding coulombic efficiency of about 100%. However, after 16 cycles at 0.1 C, the capacity is about 736 mAh $g^{-1}$, and the corresponding coulombic efficiency is only about 69.7%.

This control experiment shows that the use of the ionic liquid-based electrolyte ($PYR_{14}$TFSI-LiTFSI-PEGDME mixture, as shown in the main text of the paper) can definitely help the improvement of the electrochemical performance of GO—S based Li/S cells. On the other hand, the previous research results indicated that when using $PYR_{14}$TFSI-LiTFSI-PEGDME mixture as electrolyte in the Li/S cells with other C—S nanocomposite (not GO—S) cathodes, the capacity fading is clear. These results directly support our conclusion that the GO clearly performs very well as a means to stabilize the S in our GO—S electrode, while using ionic-liquid based electrolyte can further enhance the performance.

In summary, a novel chemical reaction-deposition method is employed to synthesize a GO—S nanocomposite to immobilize S in the cathode material of Li/S cells. The GO—S nanocomposite cathodes display good reversibility, excellent capacity stability of about 1000 mAh $g^{-1}$, and rate capability of up to 2 C in ionic liquid-based electrolyte. The GO in the heat-treated composites have good conductivity, extremely high surface-area, and provide a robust electron transport network. The functional groups on the GO surface play the role of immobilizers that keep intimate contact of the conducting matrix with S species, and effectively confine any polysulfides from dissolving. The GO network also accommodates the volume change of the electrode during the Li—S electrochemical reaction. As a result, reversibility and high rate discharge capability were obtained. The same strategy could be helpful to explore and develop new porous carbon, or conductive polymer based S nanocomposite cathodes for advanced Li/S cells.

Experimental Details

Chemicals.

Graphite powder, sodium nitrate ($NaNO_3$), potassium permanganate ($KMnO_4$), 96% sulfuric acid ($H_2SO_4$) solution, 30% hydrogen peroxide ($H_2O_2$) solution, sodium sulfide ($Na_2S$, anhydrous, Alfa Aesar), sublimed S powder (99.9%, Mallinckrodt), formic acid (HCOOH, 88%, Aldrich), N-methy-N-butylpyrrolidinium bis(trifluoromethanesulfonyl) imide ($PYR_{14}$TFSI, ≥98.0%, Aldrich), poly (ethylene glycol) dimethy ether (PEGDME, $M_w$=250, Aldrich) and lithium bis(trifluoromethylsulfonyl)imide (LiTFSI, 99.95%, Aldrich) were used without further treatment.

Synthesis of the Graphene Oxides.

The graphene oxide used in an embodiment of the invention is exfoliated from graphite oxide prepared using the following method. Graphite oxide was prepared using a modified Hummers method. Firstly, 0.2 g of natural graphite powder and 0.175 g of $NaNO_3$ were placed in a three-necked flask with a stirrer chip. Then 15 ml of 98% $H_2SO_4$ was slowly added. The mixture was stirred in an ice water bath environment for about 2 hours followed by gradually adding 0.9 grams of $KMnO_4$ (purity 99%) over about 2 hours under slow stirring conditions. The as-formed mixture was allowed to react for five days at room temperature. Afterwards, 20 ml of 5 wt % $H_2SO_4$ aqueous solution was added over the course of about 1 h with stirring. The resultant mixture was further stirred for 2 h followed by adding 0.6 ml of 30 wt % $H_2O_2$ aqueous solution and stirred for another 2 h. This solution was continuously washed thoroughly with a mixed aqueous solution of 3 wt % $H_2SO_4$/0.5 wt % $H_2O_2$ many times, and then the purification procedure was similarly repeated three more times using deionized (DI) water (Millipore, 18.2 MΩcm). The resultant mixture was dispersed in DI water and then centrifuged to remove ions of oxidant origins. The remaining dispersion was purified by repeating the same procedures 20 times with DI water. Finally, a brown-black homogeneous graphite oxide dispersion was obtained. In this embodiment, 180 mg of graphite oxide was suspended in 180 ml ultrapure water (Millipore, 18.2 MΩcm), and then sonicated at 50° C. for 5 hours to form a stable graphene oxide (GO) dispersion.

Preparation of Sodium Polysulfide Solution.

0.58 g Na$_2$S was added into a flask that has been filled with 25 ml distilled water to form a Na$_2$S solution, then 0.72 g elemental S was suspended in the Na$_2$S solution and stirred with a magnetic stirrer for about 2 hours at room temperature. The color of the solution changed slowly to orange-yellow as the sulfur dissolved. After dissolution of the sulfur, a sodium polysulfide (Na$_2$S$_x$) solution was obtained (It should be noted that through controlling the ratios of Na$_2$S and elemental S, we adjust the value of x in Na$_2$S$_x$, this will further control the S content in the as following prepared GO—S composites).

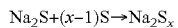

Na$_2$S+(x−1)S→Na$_2$S$_x$

Synthesis of Graphene Oxide-Sulfur Composite.

The novel graphene oxide-sulfur (GO—S) composite was prepared by a chemical deposition method in an aqueous solution. 180 mg of graphite oxide was suspended in 180 ml ultrapure water (Millipore, 18.2 MΩcm), and then sonicated at 50° C. for 5 hours to form a stable graphene oxide (GO) dispersion. Then, the Na$_2$S$_x$ solution was added to the above-prepared GO dispersions in the presence of 5 wt % surfactant cetyl trimethylammonium bromide (CTAB), the as-prepared GO/Na$_2$S$_x$ blended solution was sonicated for another 2 hours and then directly titrated into 100 ml of 2 mol/L HCOOH solution at a rate of 30~40 drops/min and stirred for 2 hours. Finally, the precipitate was filtered and washed with acetone and distilled water several times to eliminate salts and impurities. After filtration, the precipitate was dried at 50° C. in a drying oven for 48 hours.

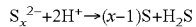

S$_x^{2-}$+2H$^+$→(x−1)S+H$_2$S

Heat treatment of GO—S composites. The as-synthesized GO—S composites were heat treated in a sealed vessel under flowing argon with controlled flow rate of about 200 cc S$^{-1}$ at 155° C. for 12 h. In order to further decrease the S content, some of the as-synthesized samples were also heat treated in the same argon environment at 160° C. for 12 h.

Cell Assembly and Testing.

CR2032-type coin cells were fabricated by sandwiching a porous polypropylene separator (Celgard 3501, Hoechst Celanese) between the heat treated GO—S nanocomposite electrode and a lithium metal foil (Cyprus Foote Mineral, 99.98%, USA) in a high-purity argon-filled glove box. 1 mol/kg LiTFSI in PYR$_{14}$TFSI/PEGDME (1:1, by weight) solution was used as the electrolyte. The GO—S working electrodes were prepared by mixing the GO—S nanocomposite, carbon black, and polyvinylidene difluoride (PVDF) at a weight ratio of 70:20:10 in NMP solvent to form a slurry. The resultant slurry was uniformly spread via doctor blade on pure aluminum foil and dried at 50° C. for 72 hours. The final S content of the cathode material is 46.2 w/o. Cyclic voltammogram (CV) measurements were performed on an AQ4 Gamry Reference 600 electrochemical workstation with a voltage range from 1.0 to 3.6 V at a scan rate of 0.05 mV s$^{-1}$. Galvanostatic discharge and charge experiments of the coin cells were conducted using an Arbin automatic battery cycler (BT-2000) at several different rates between cut-off potentials of 1.0 and 3.0 V. All of the electrochemical performance measurements were obtained at a constant temperature of 25° C.

Material Characterizations.

The samples were characterized using scanning electron microscopy (SEM: Zeiss Gemini Ultra-55) coupled with an energy dispersive X-ray spectrometer (EDX), transition electron microscope (TEM: 200 kV FBI monochromated F20 UT Tecnai), thermogravimetric analysis (TGA), X-ray diffraction (XRD) (Diffraktometer D500/501, Siemens), Hall effect measurement system (HMS-5000), Attenuated total reflection Fourier transform infrared spectroscopy (ATR-FTIR) (Nicolet Avatar 360 with an Omni-Sampler ATR accessory), and X-ray photoelectron spectroscopy (XPS) (Surface Science Instruments S-probe spectrometer). The soft X-ray absorption spectroscopy (XAS) measurements were performed on Beamline 7.0.1 at the Advanced Light Source of Lawrence Berkeley National Laboratory. The energy resolution of monochromator was set to 0.1 eV for the C K-edge and S L-edge XAS.

Computational Methods.

All the calculations were performed by using Vienna ab-initio simulation package (VASP). The Perdew-Burke-Ernzerhof (PBE) generalized gradient approximation and the projector-augmented wave (PAW) potential with a cutoff energy of 400 eV were used to describe the exchange-correlation energy and the electron-ion interaction, respectively. We adopted a 5×5 supercell geometry for graphene and the distance between two adjacent carbon sheets is at least 10 Å. A k-mesh of 6×6×1 was used to sample the Brillouin zone. All the geometries were optimized without any symmetry constraint until the residual force on each atom is less than 0.01 eV/Å. Herein, two-sided configurations are considered for adsorption on GO. The binding energy of a pair of Sulfur atoms is defined as the energy difference between the reactants (graphene/GO and two S atoms) and products (the S-adsorbed complex), that is BE=E$_{G/GO}$+2E$_S$−E$_{G/GO-2S}$. Detailed calculated results are shown in FIG. 10.

Figure 8:
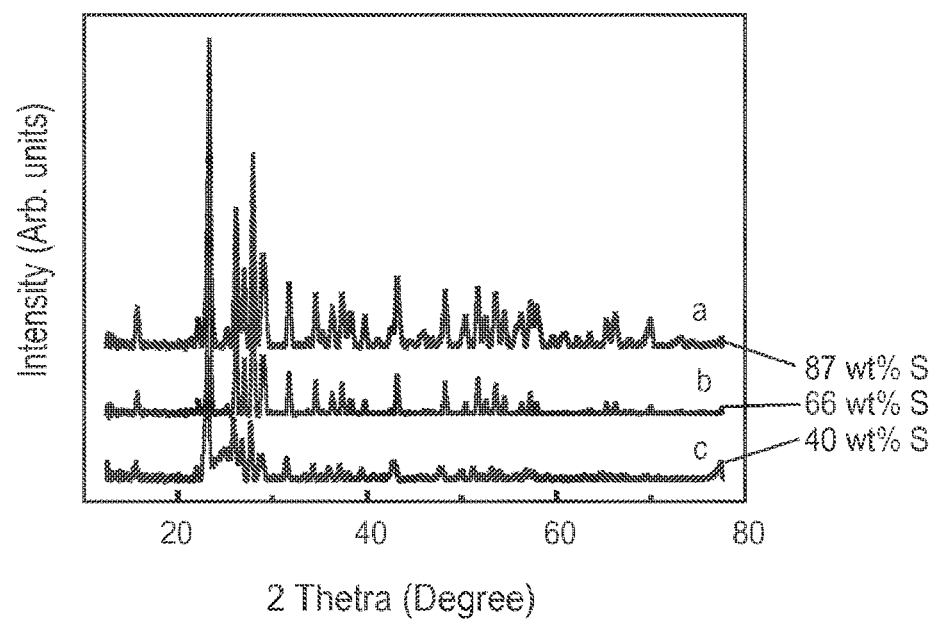
FIG. 8 illustrates X-ray diffraction (XRD) patterns of GO—S nanocomposites before (a) and after heat treatment in Ar environment for 12 h at different temperatures of (b) 155° C., and (c) 160° C. according to an embodiment of the invention.

FIG. 8 illustrates XRD patterns of GO—S nanocomposites before (a) and after heat treatment in Ar environment for 12 h at different temperatures of (b) 155° C., and (c) 160° C. The crystallized S nanoparticles were observed under the high-resolution TEM (HRTEM) imaging mode, as shown below in FIG. 17d. However, we cannot exclude the possibility that there are some larger S crystallites in the thicker region of the samples (residues of those seen in FIG. 7 before heat treatment) that could also contribute to the XRD patterns.

FIG. 10 illustrates calculated results (yellow, red and white balls denote S, O and H atoms, respectively, while the others, blue, are carbon atoms): First, we calculate two S atoms adsorption on graphene separately FIG. 10(a) and in pair FIG. 10(b). The binding energies are 1.64 and 2.08 eV, respectively, which can be viewed as the lower and higher bounds of S adsorption. Then we study the effect of adsorbed epoxy groups on the adsorption of two S atoms. It is found that S adsorption can be significantly enhanced by epoxy groups, depending on the distance between the functional group and S atom. Typically, the binding energies are 1.82 eV and 2.03 eV for the adsorption configurations shown in FIG. 10(c) and FIG. 10(d). Note that the locations of S atoms are the same as that in FIG. 10(a), where the binding energy is 1.64 eV. The enhancement effect of the epoxy decreases with increasing distance between S and the epoxy group. Additional calculations show that the hydroxyl group exhibits a similar trend. FIG. 10(e) and FIG. 10(f) give the binding energy of 1.66 and 2.84 eV, indicating that the effect of hydroxyl group is more local than that of the epoxy. A surprising result is that S atoms can also insert into the O—H bond (g), with a much larger binding energy of 4.05 eV. However, the dynamic factor may hinder its formation.

Figure 11:
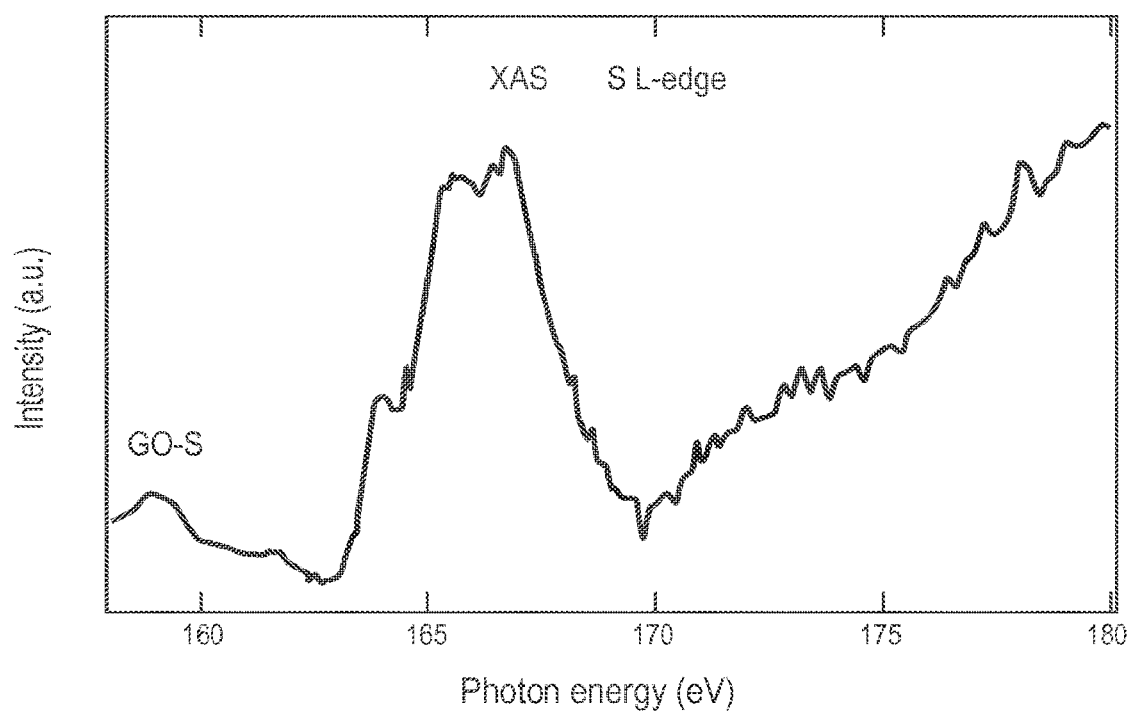
FIG. 11 illustrates S L-edge soft X-ray absorption spectroscopy (XAS) spectrum of GO—S nanocomposites after heat treatment in Ar at 155° C. for 12 hours according to an embodiment of the invention.

FIG. 11 illustrates S L-edge XAS spectrum of GO—S nanocomposites after heat treatment in Ar at 155° C. for 12 hours. It confirms the existence of S in the composites. The soft X-ray absorption spectroscopy (XAS) measurements were performed on Beamline 7.0.1 at the Advanced Light Source. The energy resolution of monochromator was set to 0.1 eV for the S L-edge XAS.

Figure 12:
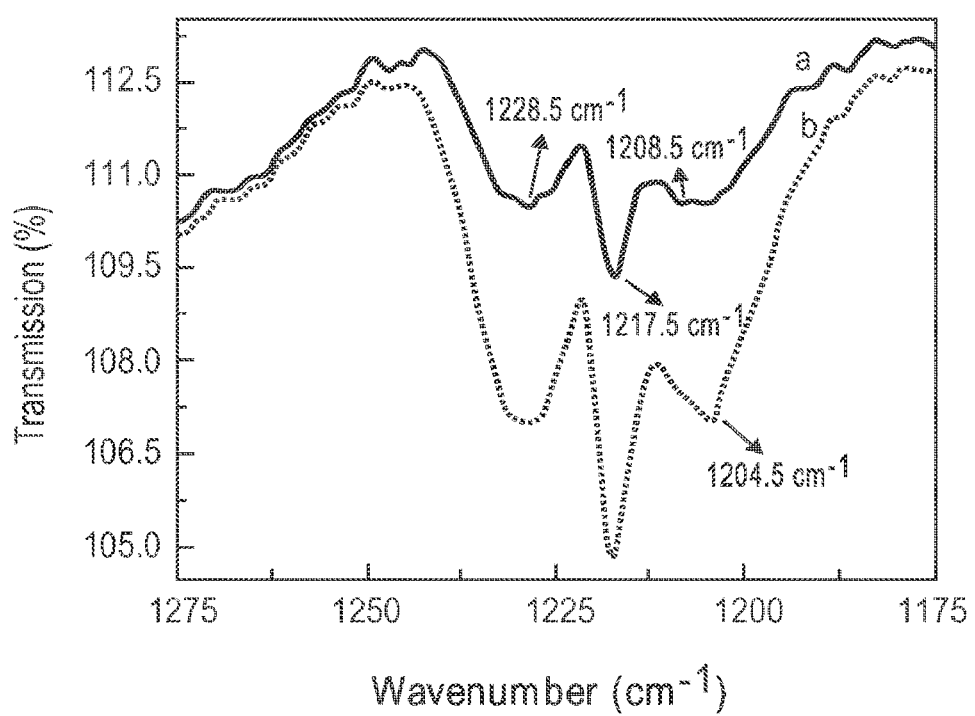
FIG. 12 illustrates fourier transform infrared spectroscopy (FTIR) spectra of (a) GO, and (b) GO—S nanocomposites according to an embodiment of the invention.

FIG. 12 illustrates FTIR spectra of (a) GO, and (b) GO—S nanocomposites. These materials were heat treated in Ar at 155° C. for 12 hours. According to the literature reports, the 1220 cm$^{-1}$ indicates the C—OH stretching vibrations, the ~1200 cm$^{-1}$ can be assigned to C—O stretch, while the characteristic feature at ~1204.5 cm$^{-1}$ in GO—S nanocomposites (while it is absent in GO) may indicate the existence of C—S bond in the as-synthesized GO—S nanocomposites after thermal treatment.

Figure 13:
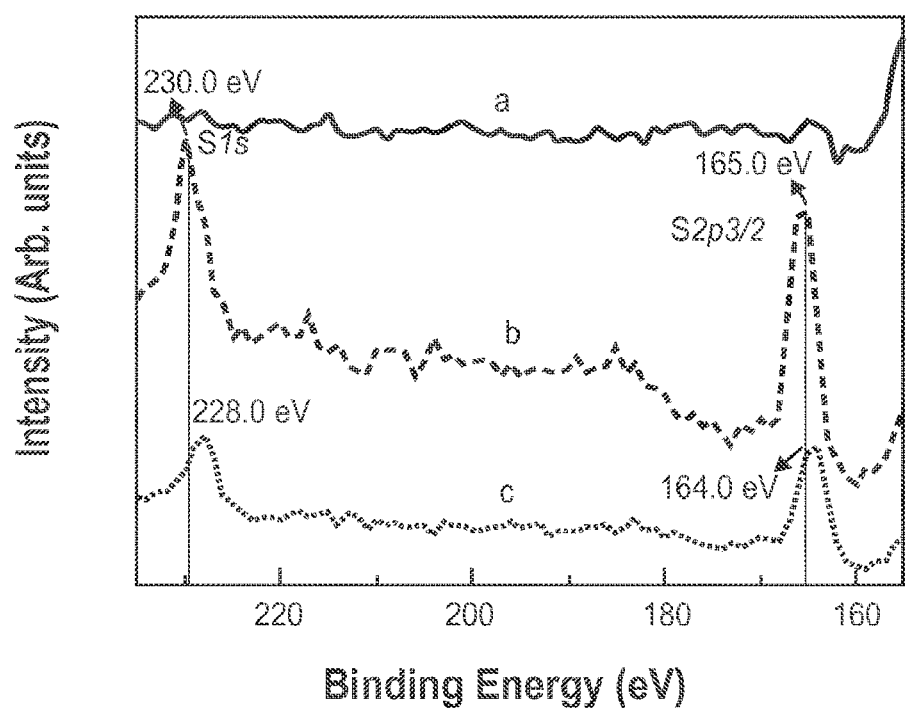
FIG. 13 illustrates X-ray photoelectron spectroscopy (XPS) spectra of (a) GO, (b) S element, and (c) GO—S according to an embodiment of the invention.

FIG. 13 illustrates XPS spectra of (a) GO, (b) S element, and (c) GO—S. The GO and GO—S were heat treated in Ar at 155° C. for 12 hours. In the S $2p_{3/2}$ region, XPS of GO—S nanocomposites show one peak at S $2p_{3/2}$ binding energy of about 164.0 eV with a slight wider full widths at half maximum intensities (FWHM) than that of elemental S. In the S 1s region, XPS of GO—S nanocomposites show one peak at S1s binding energy of about 228.0 eV with a slight wider full widths at half maximum intensities (FWHM) than that of elemental S. These chemical shifts of S$2p_{3/2}$ and S1s regions may indicate that there have interactions between S and GO in the GO—S nanocomposites.

FIG. 17 illustrates SEM (a, b) and TEM (c, d) images of the as-synthesized GO—S nanocomposites after heat treatment in Ar at 160° C. for 12 hours. In the high-resolution TEM (HRTEM) image (d), some crystallized S nanoparticles are highlighted by arrows.

FIG. 18 illustrates an electrochemical evaluation of GO—S nanocomposite cathodes made by a different process from that in the description above. The GO—S nanocomposites were heat treated in Ar at 160° C. for 12 hours. The S content in the GO—S nanocomposite was about 40 wt %, and the S content in the cathode (including carbon black and binder) was about 28 wt %. (a) CV curve of a GO—S nanocomposite cathode at 0.05 mV s$^{-1}$ scanning rate; (b) Galvanostatic charge/discharge profiles of GO—S nanocomposite cathode at 0.02 C rate; (c) cycling performance of GO—S nanocomposite cathode at a constant current rate of 0.1 C after an initial activation processes at 0.02 C for 2 cycles; (d) Reversible capacity vs. current density (rate capability) for GO—S nanocomposite cathode. All the cells were cycled in the potential window from 1.0 to 3.0 V.

Note that the capacity values are normalized to the initial discharge capacity. Also note that the first discharge capacity curve is in abnormal shape (b). We can also see an extra reduction current at lower voltage region in the first cycle of the CV curve (a). These features may come from some irreversible electrochemical reactions related to the GO, because this abnormal initial discharge is only significant in samples with lower S loading (i.e. higher GO content; we did not observe such abnormal behavior in the samples prepared using the process described above-FIGS. 4, 14, and 15). Nevertheless, these results show that GO—S (even though it is processed differently) can help to improve the capacity retention, coulombic efficiency, and rate capacity of the Li/S cells.

Figure 19:
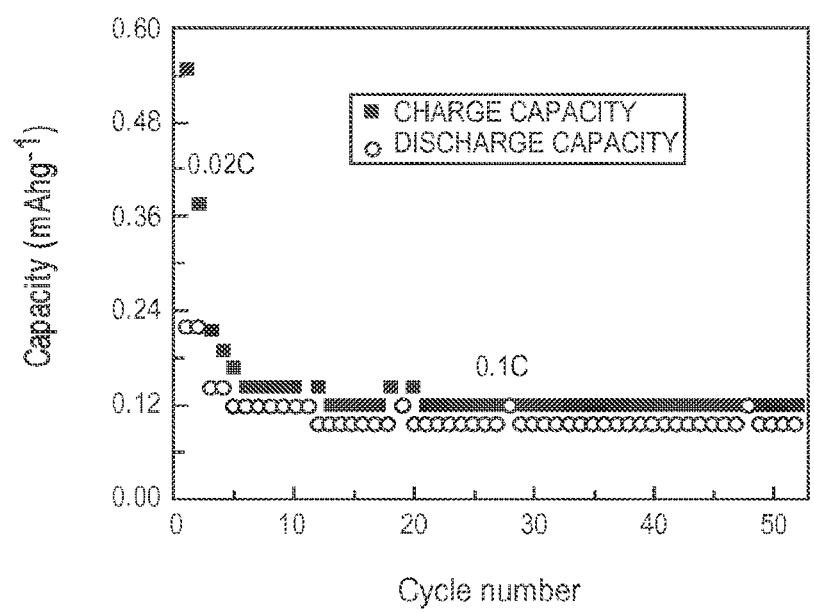
FIG. 19 illustrates cycling performance of a pure GO cathode at a constant rate of 0.1 C after an initial activation processes at 0.02 C for 2 cycles according to an embodiment of the invention.

FIG. 19 illustrates cycling performance of a pure GO cathode at a constant rate of 0.1 C after an initial activation processes at 0.02 C for 2 cycles. The GO was heat treated in Ar at 155° C. for 12 hours before assembling coin cell. The result indicates that the GO phase contributes essentially nothing to the capacity, because at the potentials of the S electrode, GO does not intercalate lithium at all.

What is claimed is:

1. A method of preparing a graphene oxide-sulfur (GO—S) nanocomposite comprising:
   providing a graphene oxide (GO) dispersion;
   adding a sodium polysulfide solution to the GO dispersion to form a blended solution;
   titrating the GO/sodium polysulfide blended solution into a HCOOH solution to form a precipitate; and
   heat treating, for a specified time and temperature, the precipitate in a sealed vessel utilizing a flowing gas at a specified gas flow rate.

2. The method of claim 1, wherein the flowing gas is argon.

3. The method of claim 1, wherein the gas flow rate is approximately 200 cc S$^{-1}$.

4. The method of claim 1, wherein the temperature is approximately 155° C.

5. The method of claim 1, wherein the time is approximately 12 hours.

6. The method of claim 1, wherein the sodium polysulfide solution is added to the GO dispersion in the presence of 5 wt % surfactant cetyl trimethylammonium bromide (CTAB).

7. The method of claim 1, wherein the sodium polysulfide solution is prepared by adding Na$_2$S into a flask that has been filled with distilled water to form a Na$_2$S solution, then elemental S is suspended in the Na$_2$S solution, wherein the ratios of Na$_2$S and elemental S, are adjusted to determine a value of x in Na$_2$S$_x$ of the sodium polysulfide solution.

8. The method of claim 7, wherein the GO after the heat treatment comprises approximately 50-90 wt % S.

9. The method of claim 8, wherein the GO after the heat treatment comprises approximately 60-70 wt % S.

10. The method of claim 1, wherein the graphene oxide (GO) dispersion is prepared by exfoliating GO from a graphite oxide.

11. The method of claim 10, wherein the graphite oxide was prepared using a modified Hummers method.

* * * * *